(12) United States Patent
Tokiwa et al.

(10) Patent No.: US 6,846,457 B1
(45) Date of Patent: Jan. 25, 2005

(54) AUTOMATIC ANALYSIS APPARATUS, MANAGING APPARATUS FOR ANALYSIS APPARATUS, AND PROGRAM PRODUCT FOR MANAGING ANALYSIS APPARATUS

(75) Inventors: Yukie Tokiwa, Hitachinaka (JP); Kyoko Imai, Hitachinaka (JP); Shigeki Matsubara, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 684 days.

(21) Appl. No.: 09/593,956

(22) Filed: Jun. 15, 2000

(30) Foreign Application Priority Data

Jun. 16, 1999 (JP) ............................................ 11-169499

(51) Int. Cl.⁷ .............................................. G01N 31/00
(52) U.S. Cl. ............................ 422/67; 422/63; 422/65; 436/47; 436/43; 436/50; 364/528
(58) Field of Search .............................. 422/67, 63, 65; 436/47, 43, 50; 364/528.01

(56) References Cited

U.S. PATENT DOCUMENTS

| 4,873,633 | A | | 10/1989 | Mezei et al. | |
|---|---|---|---|---|---|
| 5,492,831 | A | | 2/1996 | Ranger | |
| 5,532,941 | A | | 7/1996 | Lin | |
| 5,565,364 | A | | 10/1996 | Schaefer et al. | |
| 6,080,364 | A | * | 6/2000 | Mimura et al. | ................ 422/67 |

FOREIGN PATENT DOCUMENTS

| EP | 0871034 | 10/1998 |
|---|---|---|
| JP | 10-2902 | 1/1998 |
| JP | 10-002902 | 1/1998 |
| WO | 95/05590 | 2/1995 |

* cited by examiner

Primary Examiner—Jill Warden
Assistant Examiner—Sam P. Siefke
(74) Attorney, Agent, or Firm—Mattingly, Stanger & Malur, P.C.

(57) ABSTRACT

An automatic analysis apparatus containing a plurality of measurement channels used to measure reaction occurred in a reaction container into which both a reagent and a sample are entered, is arranged by employing: a data processing unit for producing calibration information, first quality control information, and second quality control information; the calibration information every measurement channel being produced based upon calibration data obtained by measuring a calibration sample, the first quality control information related to a quality for each of the measurement channels being produced based upon measurement data acquired by measuring a quality controlling sample by the respective measurement channels, and also the second quality control information related to an entire quality of the plural measurement channels being produced based upon the measurement data; and a display unit for simultaneously displaying the calibration information, the first quality control information, and the second quality control information given by the data processing unit on a single screen.

11 Claims, 7 Drawing Sheets

FIG.7

| MEASUREMENT CHANNEL 13-1 | | | | MEASUREMENT CHANNEL 13-2 | | COUNTERMEASURE |
|---|---|---|---|---|---|---|
| CALIBRATOR #1 | CALIBRATOR #2 | CALIBRATOR #1/ CALIBRATOR #2 | | CALIBRATOR #1 | CALIBRATOR #1/ CALIBRATOR #2 | |
| | | | CALIBRATOR #2 | | | |
| OK | OK | OK | OK | LEVEL 2 | LEVEL 2 | EXECUTE CONDITIONING (MAINTENANCE #1) OF DETECTION UNIT D2 |
| OK | OK | OK | LEVEL 2 | LEVEL 2 | LEVEL 2 | EXECUTE CONDITIONING (MAINTENANCE #1) OF DETECTION UNIT D2 EXECUTE AIR PURGING OF REAGENT PIPETTING MECHANISM R2 AND SAMPLE PIPETTING MECHANISM S2 |
| LEVEL 2 | OK | LEVEL 2 | OK | LEVEL 2 | LEVEL 2 | EXECUTE CONDITIONING (MAINTENANCE #1) OF DETECTION UNITS D1 & D2 |
| ----- | ----- | ----- | ----- | ----- | ----- | ----- |

80

AUTOMATIC ANALYSIS APPARATUS, MANAGING APPARATUS FOR ANALYSIS APPARATUS, AND PROGRAM PRODUCT FOR MANAGING ANALYSIS APPARATUS

BACKGROUND OF THE INVENTION

The present invention generally relates to an automatic analysis apparatus, and more specifically, is related to an automatic analysis apparatus suitably for measuring the same analysis item in a plurality of measuring channels with respect to a large number of samples, is also related to a managing apparatus, and a program product for managing data quality of the analysis apparatus.

Very recently, strong needs are made in automatic analysis apparatuses. That is, since processing capabilities of such automatic analysis apparatuses are wanted to be increased, a large amount of samples can be analyzed within a short time period. Under such a circumstance, the following automatic analysis apparatuses have been marketed in which a plurality of analysis modules are connected so as to measure reaction fluids, while pipetting both reagents and samples into reaction containers.

As automatic analysis apparatuses, there are biochemical analysis apparatuses, immunity analysis apparatuses and so on. As analysis items of a biochemical analysis apparatus, cholesterol density (concentration) contained in a blood sample is measured, either a GPT value or a blood sugar level contained in a blood sample is measured, and protein density contained in a urine sample is measured. Such an analysis is carried out as follows. That is, for instance, while a sample to be measured and a preselected reagent are put into a reaction container, both the sample and the reagent may cause opto-chemical reaction, so that a photodetector may detect an amount of specific light emitted from this opto-chemical reaction, or a spectral analyzer analyzes a spectrum of light which passes through the reaction fluid. Then, an electric signal produced from the photodetector is converted into density values of analyzed components by using a calibration curve. An automatic analysis apparatus is capable of measuring a plurality of these analysis items in a continuous manner as to an individual sample of large amounts of samples.

In this case, precision in the respective elements employed in such an automatic analysis apparatus, for instance, pipetting of the sample/reagent and detections of the electric signals from the reaction fluid, could give adverse influences to the measurement values. As a result, if the route paths of the automatic analysis apparatus defined from pipetting of the sample/reagent up to measuring of the reaction fluid are made different from each other, then the resultant measurement data may contain a difference caused by the route paths of analysis through which the measurement data are obtained even when the same analysis item is measured.

As explained above, when a plurality of measurement data about the same analysis item are acquired via the different route paths, the respective route paths are called as "measurement channels" which are discriminatable.

In the above-explained automatic analysis apparatus in such a case that a plurality of different analysis items are analyzed within one time, the different, or separate analysis items may be allocated to the respective measurement channels. Alternatively, a large sampling number of analysis items may be shared by a plurality of measurement channels so as to be measured. Conventionally, the calibration results and the quality control results for data accuracy and reliability are separately managed with respect to each of these measurement channels in the automatic analysis apparatuses.

A calibration is obtained in the form of either a calibration curve or line in such a manner that while two or more samples having known different densities of a component are analyzed by an analysis apparatus, a relationship between analysis output signals and the known density values is expressed as such a calibration curve, or a calibration line. A quality control is utilized so as to maintain measurement precision and reliability of an analysis apparatus in such a manner that while a sample having known density is measured by the analysis apparatus for either a constant time period or an irregular time period, measurement data acquired in a time sequential manner are processed by way of the statical manner so as to detect a data variation and a data fluctuation.

In the automatic analysis apparatus described in JP-A-10-2902, at least two sets of the analysis items of the measurement samples and also the information related to this analysis item are displayed on a single screen by the information display management means, so that a plurality of information can be confirmed within one time.

In an automatic analysis apparatus equipped with a plurality of measurement channels, more specifically, even in such an automatic analysis apparatus for measuring the same analysis item in a plurality of measurement channels, the individual equipped measurement results can be considered as the measurement result acquired from a single automatic analysis apparatus. In other words, even when the same analysis item is measured by any of the measurement channels, it is important to obtain measurement data having a same accuracy level.

To this end, the respective measurement channels for measuring the same analysis item must be maintained under same measurement precision condition. This measurement precision may be similarly applied to such a case that a single analysis module is equipped with a plurality of measurement channels.

For example, there is a system wherein a pipetting mechanism of a sample and a pipetting mechanism of a reagent are commonly used in different channels, and while different detection units are used for the channels. There is another case that different pipetting mechanisms of a sample, or a reagent are used, and while a single signal detecting unit is commonly used in different channels.

In the case that the same analysis item is measured by such plural measurement channels, the calibration is individually, or separately carried out as to the respective measurement channels. When the calibration results of this same analysis item are managed every measurement channel, for example, even if the data about the calibration results for a plurality of different analysis items measured in this measurement channel are collected and then are displayed on the screen, this display method is not suitable for systematically grasping both the measurement precision and the measurement reliability of the same analysis item as the entire analysis apparatus. In other words, this display method is not proper when measurement precision of a certain measurement channel is compared with that of another measurement channel. Moreover, confirmations of the calibration results of a plurality of measurement channels may become cumbersome. This cumbersome confirmation may cause the work load of the user to be increased, while a total number of measurement channels is increased.

Similar to such a quality control executed in the case that measurement data are acquired from a single measurement channel, a quality control must be carried out as follows. That is, in addition to a quality control executed in an individual measurement channel, various measurement data are gathered together as a single measurement data group without being discriminated from each other. These measurement data are acquired from the respective measurement channels through which the same analysis item is measured by using each of these analysis modules, or the entire analysis apparatus.

As a consequence, such a confirmation can be made as to such a case that although the quality control data of each of the measurement channels may satisfy the allowable value of the quality control, such quality control data obtained by combining the measurement data of the plural measurement channels cannot satisfy the allowable value.

In the automatic analysis apparatus described in JP-A-10-2902, the measurement data of the plural measurement channels may be displayed on a single screen.

However, in such a case that even when the quality control data may satisfy the allowable range, the quality control data as the entire analysis apparatus cannot satisfy the allowable range, this automatic analysis apparatus cannot automatically judge this quality control data. As a consequence, the quality control as the entire automatic analysis apparatus can be hardly realized.

If the calibration information of the respective measurement channels could be displayed as a list in combination with the above-explained quality control information, then such information by which the user of the automatic analysis apparatus can judge the conditions of the respective measurement data could be provided within one time. As a result, the user can easily grasp the conditions of the automatic analysis apparatus.

SUMMARY OF THE INVENTION

An object of the present invention is to provide an automatic analysis apparatus capable of judging not only quality control information of each of plural measurement channels contained in a single set of such automatic analysis apparatus, but also capable of judging precision of the entire analysis apparatus to thereby display the judged quality control information and further the judged precision, and capable of readily grasping a condition of the own automatic analysis apparatus.

An automatic analysis apparatus, according to an aspect of the present invention, is featured by comprising: a plurality of measurement channels for measuring reaction occurred in a reaction container for containing thereinto both a reagent and a sample; a data processing unit for producing calibration information, first quality control information, and second quality control information; the calibration information every measurement channel being produced based upon calibration data obtained by measuring a calibration sample, the first quality control information related to a quality for each of the measurement channels being produced based upon measurement data acquired by measuring a quality controlling sample by the respective measurement channels, and also the second quality control information related to an entire quality of the plural measurement channels being produced based upon the measurement data; and a display unit for simultaneously displaying the calibration information, the first quality control information, and the second quality control information given by the data processing unit on a single screen.

An automatic analysis apparatus, according to an embodiment of the present invention, is arranged as follows:

(1) In an automatic analysis apparatus for pipetting both a reagent and a sample into a reaction container and for measuring a reaction fluid produced by pipetting the reagent and the sample, the automatic analysis apparatus includes a plurality of measurement channels for measuring the same analysis item; calibration information, quality control information for each of the measurement channels, and quality control information for the entire automatic analysis apparatus are displayed on a screen of a display apparatus in a batch mode. The calibration information every measurement channel is produced based upon calibration data obtained by measuring a calibration sample, the quality control information for each of the measurement channels is produced based upon measurement data acquired by measuring a quality controlling sample by the respective measurement channels, and also the quality control information related to the entire analysis apparatus is produced based upon the measurement data.

(2) In the above-explained automatic analysis apparatus (1), preferably, a plurality of levels are previously set as the calibration information and/or an allowable value of the quality control information.

(3) In the above-described automatic analysis apparatus (2), preferably, a judgment is made as to whether or not the calibration information measured in the measurement channels can satisfy each of the allowable values. When the calibration information can satisfy the allowable value, a shift from the allowable value is calculated, and a level equivalent to the measured calibration information is displayed.

(4) In the above-described automatic analysis apparatus (2), preferably, a judgment is made as to whether or not the quality control information measured in the measurement channels can satisfy each of the allowable values. When the quality control information can satisfy the allowable value, a shift from the allowable value is calculated, and a level equivalent to the measured quality control information is displayed.

(5) In the above-described automatic analysis apparatus (2), preferably, a judgment is made as to whether or not the calibration information measured in the measurement channels can satisfy each of the allowable values. When the calibration information can satisfy the allowable value, a deviation from the allowable value is calculated, and levels equivalent to the measured calibration information are displayed respectively in different colors from colors of peripheral display contents.

(6) In the above-described automatic analysis apparatus (2), preferably, a judgment is made as to whether or not the quality control information measured in the measurement channels can satisfy each of the allowable values. When the quality control information can satisfy the allowable value, a shift from the allowable value is calculated, and levels equivalent to the measured quality control information are displayed respectively in different colors from colors of peripheral display contents.

(7) In the above-described automatic analysis apparatus (2), preferably, various combined levels and messages indicative of countermeasure processes corresponding to these levels are previously stored. These levels are given in the case that a plurality of measurement channels and/or each of these measurement channels used to measure the same analysis item cannot satisfy the allowable values of the quality control information, and in such a case that the above-explained calibration information can satisfy the allowable value. A judgment is made as to whether or not a plurality of measurement channels and/or each of these measurement channels used to measure the same analysis item can satisfy the allowable values of the quality control information. When these measurement channels cannot satisfy the allowable values of the quality control information, such a message indicative of the relevant solution process is displayed.

With employment of the above-described arrangement, in the automatic analysis apparatus having a plurality of measurement channels, not only the quality control information of the respective measurement channels is displayed, but also the quality control information is displayed which is acquired based upon the measurement data obtained by measuring the same analysis item in a plurality of measurement channels. In other words, the quality control information of the entire analysis apparatus for combining these individual measurement channels with each other may also be displayed. As a consequence, the user can recognize such a case that although the measurement quality allowable range can be satisfied in the respective measurement channels, the measurement quality allowable range cannot be satisfied in the entire analysis apparatus.

Also, since the calibration information of the respective channels is additionally displayed, the condition of the automatic analysis apparatus can be grasped.

Furthermore, in such a case that although the measurement quality allowable range can be satisfied in the respective measurement channels, the measurement quality allowable range cannot be satisfied in the entire analysis apparatus, such a solution process message is displayed. As a result, the measurement quality control of the automatic analysis apparatus can be readily carried.

BRIEF DESCRIPTION OF THE DRAWINGS

For a better understanding of the present invention, reference is made of a detailed description to be read in conjunction with the accompanying drawings, in which:

FIG. 7 is a table for representing contents of maintenance with respect to each of level combinations of calibration data stored in a data processing unit of the automatic analysis apparatus shown in FIG. 1.

DESCRIPTION OF THE EMBODIMENTS

An embodiment mode of the present invention will now be described.

Figure 1:
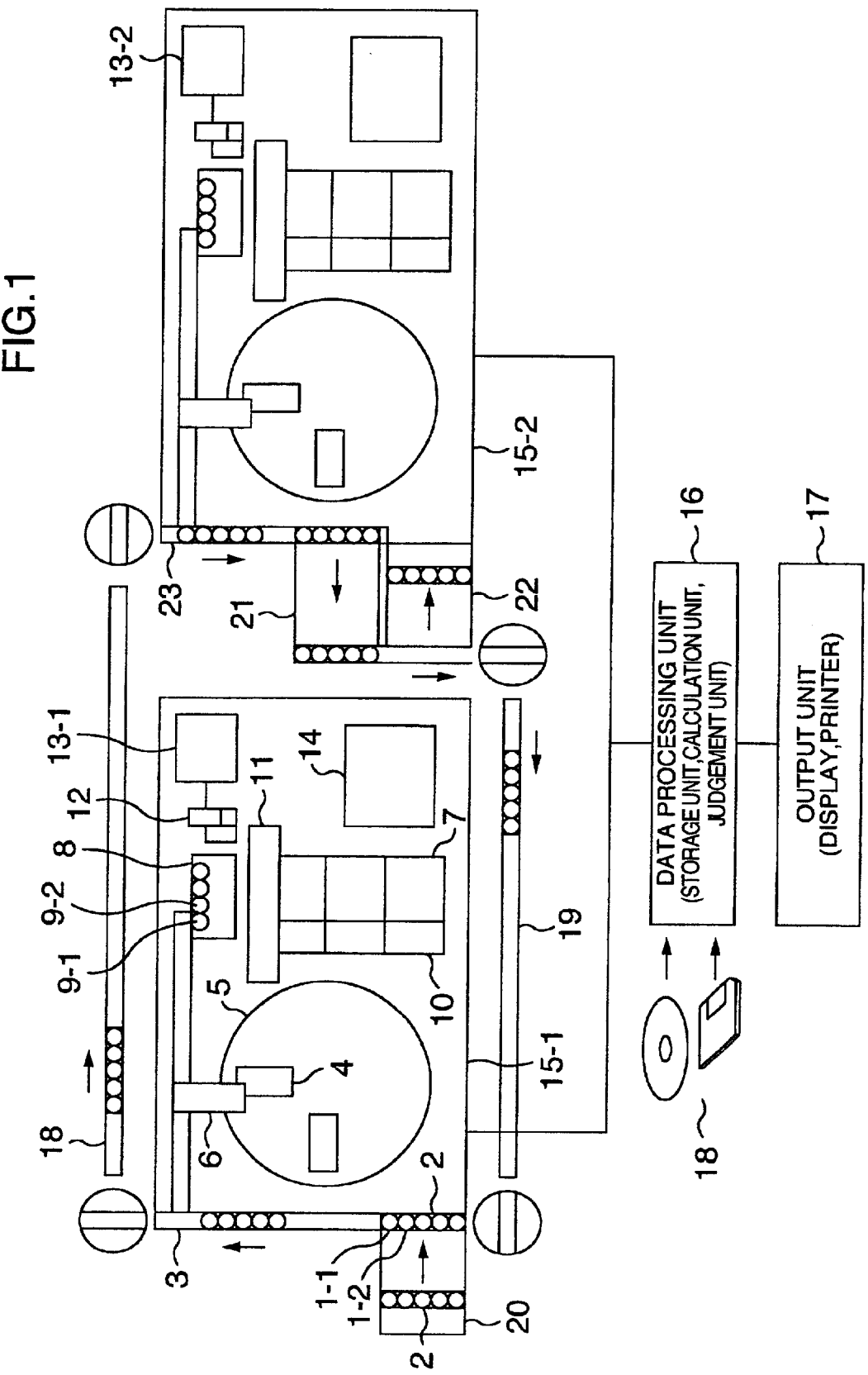
FIG. 1 is a plan view for representing an entire structure of an automatic analysis apparatus according to an embodiment mode of the present invention.

FIG. 1 is an entire structural diagram of an automatic analysis apparatus according to an embodiment mode of the present invention.

In FIG. 1, an analysis module 15-1 is provided with an examination sample inserting unit 20 and a convey path 3. The examination sample inserting unit 20 feeds a rack 2 capable of installing a plurality of sample containers 1-1, 1-2, - - - , which contain thereinto samples. The samples contained in the sample containers 1-1, 1-2, - - - , may be conveyed up to a sampling position of the analysis module 15-1. While the samples are transported in a half way of this convey path 3, such information related to a quality control sample used to measure a sort of a sample and a lot of the sample is registered into a data processing unit 16 from bar codes attached to the sample containers 1-1, 1-2, - - - , by way of a bar code reader (not shown).

A reagent 4 is set on a reagent disk 5, and information such as a sort of a reagent and a lot of the reagent is also registered into the apparatus via a bar code. Pipettings of a sample and a reagent are carried out by a pipetting probe 6. Every time either a sample or a reagent is pipetted, a disposable tip is mounted/released on/from a tip portion of the pipetting probe 6, an unused tip is held on the rack 7. An incubator 8 holds a plurality of reaction containers 9-1, 9-2, - - - .

The reaction containers 9-1, 9-2, - - - , are disposable, and unused reaction containers 91-, 9-2, - - - , are held on the rack 10. Both the reaction containers 9-1, 9-2, - - - , and the tips are transported by a transport mechanism 11. The used tips and the used reaction containers are discarded at one place.

A reaction fluid contained in a reaction container is conducted from a nozzle 12 to a detector employed in a detection unit 13-1, and then a light emission amount from the reaction fluid is detected by the detector. The reaction fluids which have been measured are collected into a waste water tank 14. An analysis module 15-1 is connected to an analysis module 15-2 by a convey path 18 of a sample and also another convey path 19 used to remeasure a sample.

In the analysis module 15-2, both a reexamination sample waiting unit 21 and an examination sample collecting unit 22 are provided, and are connected to a convey path 23 for conveying a sample along a direction opposite to that of the convey path 3. Other remaining structures of this analysis module 15-2 are similar to those of the analysis module 15-1. The signals detected by the detection unit 13-1 and the detection unit 13-2 are converted into density values (concentration values) by a data processing unit 16 based upon a calibration curve. Then, this measurement result is supplied to an output unit 17.

The data processing unit 16 may be realized by a general-purpose computer. A computer for constituting the data processing unit 16 is arranged by containing a CPU operated in accordance with a program, a ROM for previously storing predetermined data and the program, a RAM for temporarily storing data and a portion of the program, an input/output port for controlling transmission/reception of a signal to/from an external unit, and a bus for coupling these devices in the computer with each other. It should be noted that both a control program of the automatic analysis apparatus according to the present invention and a program for a quality control may be stored into a recording medium 18 such as an optical disk and a flexible disk in a computer readable code format, and these programs may be downloaded to a memory device of the computer.

Next, a description will now be made of a measuring operation example of a sample in the automatic analysis apparatus according to an embodiment mode, shown in FIG. 1.

The automatic analysis apparatus, according to the embodiment mode of the present invention, measures calibrators 1 and 2 of an analysis item "A" having different density from each other, or the analysis item "A" of quality control samples 1 and 2. These calibrators 1 and 2 for certain examination samples are stored into the sample contains 1-1 and 1-2, respectively. The sample containers 1-1 and 1-2 are set to the rack 2 for conveying the sample. The analysis item "A" corresponds to, for example, cholesterol, blood sugar level or other chemical component analysis. A calibrator corresponds to a sample having known density component used to measure a calibration curve.

First, the sample container 1-1 which stores thereinto either the calibrator 1 or the quality control sample 1 is conveyed from the examination sample inserting unit 20 via the convey path 3 to a sampling position of the analysis module 15-1. Next, the pipetting probe 6 mounts the disposable tip on the tip portion, and pipets both a reagent and a sample into the reaction container 9-1 positioned at the pepetting position. The disposable tip is positioned by the transport mechanism 11 to the tip mounting position. The reaction container 9-1 into which both the reagent and the sample are pipetted is transported by the transport mechanism 11 onto the incubator 8.

When the reaction for a first step is accomplished, the reagent 4 set to the reagent disk 5 is pipetted by the pipetting probe 6 into the reaction container 9-1, and subsequently is stirred. After the reaction between the reagent 4 and the sample is completed, the reaction container 9-1 is transported by the transport mechanism 11 to the suction position by the nozzle 12. The reaction fluid stored in the reaction container 9-1 is conducted to the detector employed in the detection unit 13-1 by way of the suction force of the nozzle 12, and then, the detector detects an amount of light emitted from the reaction fluid. After one sample has been measured, the inside portion of the detector is cleaned up, and then, the next measurement is prepared.

To perform a dual measurement by a calibrator, after the pipetting probe 6 pipets a first calibrator from the sample container 1-1 to the reaction container 9-1, the tip of the tip portion is replaced by another tip, and then, the pipetting probe 6 again pipets the first calibrator from the sample container 1-1 to the reaction container 9-2. Thereafter, while the tip of the tip portion is replaced by another tip, the pipetting probe 6 pipets a second calibrator contained in the sample container 1-2 conveyed to the sampling position into the reaction container in a similar manner to that of the first calibrator. This reaction container is sequentially processed in a similar process operation of the reaction container 9-1.

In the case that either a quality control sample is measured or a regular analysis sample (regular component analysis) is measured, after either a quality control sample "a" or a general examination sample stored in the sample container 1-1 has been pipetted, the tip of the tip portion is replaced by another tip, and then either a quality control sample "b" or a general examination sample stored in the sample container 1-2 conveyed to the sampling position is pipetted into the reaction container 9-2. The reaction container 9-2 is sequentially processed in a similar process operation of the reaction container 9-1.

In such a case that as to a single piece of a regular examination sample, a plurality of analysis items are analyzed by using a single set of analysis module, after the general examination sample stored in the sample container 1-1 has been pipetted into the reaction container 9-1, the tip of the tip portion of the pipetting probe 6 is replaced by another tip. Then, the general examination sample is again pipetted from the sample container 1-1 into the reaction container 9-2.

The rack 2 in which the sampling operation has been completed by the analysis module 15-2 is conveyed via the convey path 18 to the analysis module 15-2. The analysis module 15-2 also performs the measurement of either a calibrator or a quality control sample in a similar analysis operation to that of the analysis module 15-1.

The rack 2 in which the sampling operation is accomplished is conveyed to the reexamination sample waiting unit 21. In this reexamination sample waiting unit 21, a measurement result is obtained. As a result, when the remeasuring operation is required, the rack 2 is entered through the convey path 19 into the convey path of the analysis module 15-1. To the contrary, when the remeasuring operation is not required, the rack 2 is collected by the examination sample collecting unit 22.

Figure 4:
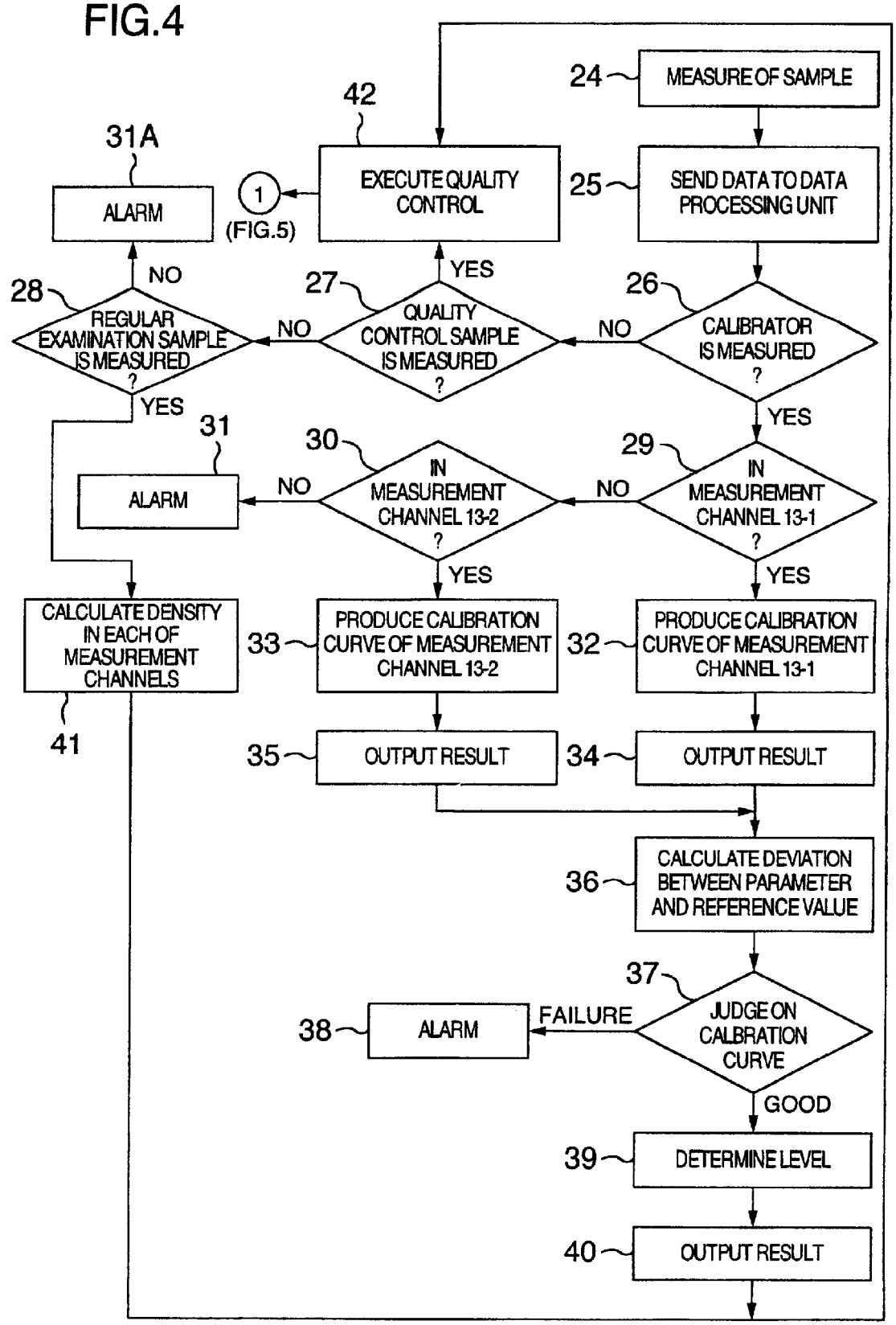
FIG. 4 is a flow chart for describing a process flow operation of measurement data in the automatic analysis apparatus indicated in FIG. 1.

FIG. 4 is a flow chart for describing a process flow operation of measurement data in the automatic analysis apparatus of FIG. 1 according to the embodiment mode of the present invention, namely a process flow operation of data for measuring a quality control sample.

The analysis modules 15-1 and 15-2 are equipped with a detection unit 13-1 and a detection unit 13-2, respectively. The respective detection units 13-1 and 13-2 measure an analysis item "A", respectively. In this case, the following designation is previously made as follows. The same calibrator is measured by measurement channels (will be referred to as "measurement channels" hereinafter), which are represented as the detection units 13-1 and 13-2.

Alternatively, in the respective measurement channels for measuring the item A, the same calibrator is measured without any designation.

When the measurement channel for measuring a calibrator is determined, the analysis module 15-1 first performs the calibrator (namely, a sample used in calibration) measurement (step 24).

Next, when the calibrator "#1" is measured in the measurement channel 13-1 in accordance with the above-explained operation, this measurement signal and information related to this measurement signal are supplied to the data processing unit 16 (step 25). As the above-explained information, there are information read from a bar code, a discrimination of measured channel, measured time, and so on.

All of signals detected by the two measurement channels 13-1 and 13-2 are acquired by the data processing unit 16, and then are stored into a storage unit of this data processing unit 16. The following process operation is determined in accordance with a sort of sample which produces this signal. In other words, a check is made at a step 26 as to whether or not a calibrator is measured based upon the data of the bar code. If the calibrator measurement is not carried out, then another check is made at a step 27 as to whether or not a quality control sample is measured at a step 27. When it is so judged at the step 27 that the quality control sample is measured, the process operation is advanced to a step 41. At this step 41, the quality control is executed.

Also, when it is so judged that the quality control sample is not measured at the step 27, another check is made at a step 28 as to whether or not the measurement sample is a regular examination sample. When it is so judged that the regular examination sample is not measured, the automatic analysis apparatus produces an alarm at a step 31A. To the contrary, when it is so judged at the step 28 that the sample is the regular examination sample, the process operation is advanced to a step 41. At this step 41, a density (concentration) calculation is carried out with respect to each of measurement channels. At a step 42, the quality control is executed.

When it is so judged at the step 26 that the calibrator is measured, the process operation is advanced to a step 29. At this step 29, another check is made as to whether or not the calibrator is measured in the measurement channel 13-1. When it is so judged that the calibrator is not measured in the measurement channel 13-1, another check is made at a step 30 as to whether or not the calibrator is measured in the measurement channel 13-2. Then, when it is so judged that the calibrator is not measured in the measurement channel 13-2, the automatic analysis apparatus produces an alarm at a step 31.

In the case that the calibrator is measured in either the measurement channel 13-1 or the measurement channel 13-2 at the step 29 or the step 30, a signal obtained by measuring the calibrator is used in the calculation unit of the data processing unit 16 so as to calculate such a calculation parameters as a gradient (inclination) of a calibration curve (calibration line) and coefficients every measurement channel through which the signal is detected. Then, a calibration curve of the analysis item "A" is formed in each of the measurement channels (steps 32 and 33).

The calibration information is outputted to the output unit 17 in combination with information of another measurement channel (step 34 and step 35). The calibration information involves a value (light emission value and spectral absorbance) of a detected signal, a calculated calculation parameter, date/time when the signal is measured, a reagent used in a measurement, and a lot of a calibrator.

Figure 2:
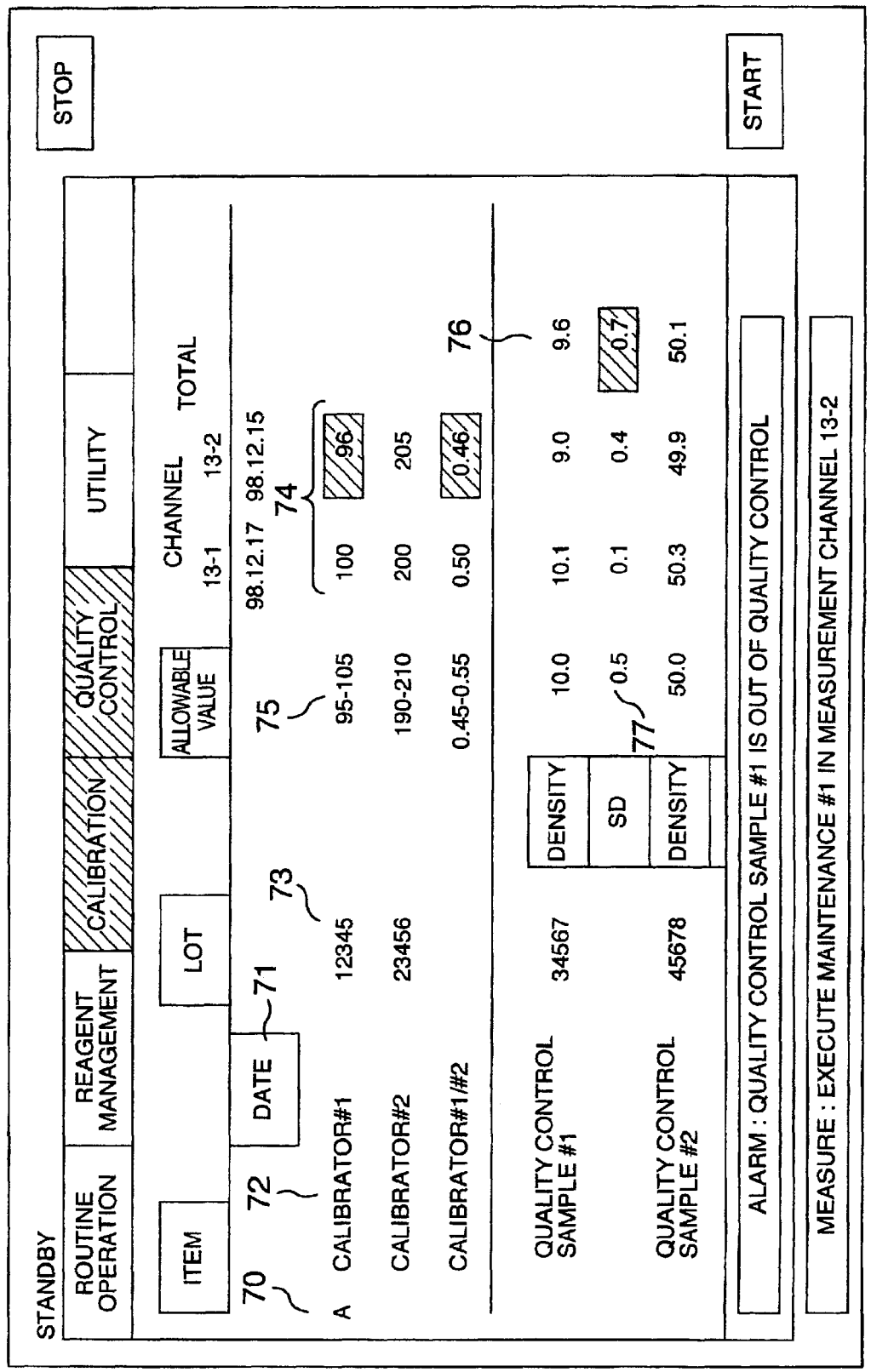
FIG. 2 is a diagram for indicating a display example of both calibration information and quality control information of two measurement channels in the automatic analysis apparatus shown in FIG. 1.

For instance, the calibration information is outputted to a preselected column of each of the measurement channels contained on the same table displayed on the display screen (see FIG. 2). In the embodiment mode shown in FIG. 1, one analysis item is measured. Alternatively, in such a case that a plurality of same analysis items are measured in each of these measurement channels, the information of other measurement channels every analysis item may be observed in the form of a list. Otherwise, the respective items may be continuously outputted.

At the next step 36, with respect to the formed calibration curve, the calculation parameters are compared with allowable values thereof, namely a shift (deviation) between measurement values of a detected signal in a dual measurement mode is compared with an allowable shift value thereof, an inclination of the calibration curve is compared with an allowable inclination value thereof, a signal value obtained under density of 0 is compared with an allowable signal value thereof, and a lower detection limit value is compared with an allowable lower detection limit value thereof. In other words, a calculation is made of a shift between the calculation parameter and the allowable value (reference value).

Then, a judgement is made at a step 37 as to whether or not the measured calibration curve is an acceptable calibration curve. When it is so judged at the step 37 that the measured calibration curve is not such an acceptable calibration curve, this fact is notified as an alarm to the output unit 17 (step 38).

As a result of the allowable judgement defined at the step 37, when the measured calibration curve can satisfy the respective allowable values, while a plurality of levels are previously determined based upon a difference between the resultant calculation parameter value and the allowable value, or a ratio of the resultant calculation parameter value to the allowable value, the following judgement is made at a step 39. That is, precision (quality) of the resultant calculation parameter belongs to which level. The judgement result is outputted (step 40). Then, after a predetermined time period (time) has passed, the process operation is advanced to a further step 42. At this step 42, a quality control sample having known density is measured in the measurement channel.

At the step 40, since a color to be displayed is changed in accordance with the level of the above-explained calculation parameter, it is possible to grasp how degree, the formed calibration curve is deviated from the allowable value. Also, a user may previously designate a level in a shift between a resultant calculation parameter and an allowable value with respect to each of analysis items.

For example, in the case that a calibration line is equal to a straight line, an inclination (gradient) of the calibration line is calculated based upon a signal value of a first calibrator #1, a signal value of a second calibrator #2 having different density from that of the first calibrator #1, and the known density of the respective calibrators. At this time, the following setting condition is assumed. That is, the calculated inclination of the calibration line may satisfy the allowable value in such a case that this calculated inclination is entered into such a range shifted by "b" from an allowable value "a" of an inclination.

A calculation is made of a difference "r" between the calculated inclination "k" and the allowable value "a". When this difference "r" is entered into such a range defined by $-b<r<b$, the inclination "k" may satisfy the allowable value.

Next, it is so assumed that when the difference "r" between the calculated inclination "k" and the allowable value "a" is equal to "c", a level 1 is set, whereas when the difference "r", between the calculated inclination "k" and the allowable value "a" is equal to "d", a level 2 is set ($0<c<d<b$). A judgement is made as to whether or not the difference "r" between the inclination "k" and the allowable value "a" becomes equal to $-c<r<c$. When the difference "r" may satisfy this condition, the level 1 is set. To the contrary, when the difference "r" may not satisfy this condition, the level 2 is set. Furthermore, one case of $-c<r$ may be discriminated from another case of $r<c$. Alternatively, one case of $-d<r$ may be discriminated from another case of $r<d$.

Also, the timing when the calibration of the same analysis item is carried out may be made different from each other, depending upon the measurement channel. In this case, both a newly measured signal and information related to this newly measured signal are outputted instead of the previously measured signal/information. The calibration information of a range designated in the preceding measurement, or the past measurement is outputted into, for example, another table having a similar format. Alternatively, while the calibration information is indicated in an ordinate and the measurement time is indicated in an abscissa, this calibration information may be displayed in the same graph as calibration information of another measurement channel (see FIG. 3).

Figure 3:
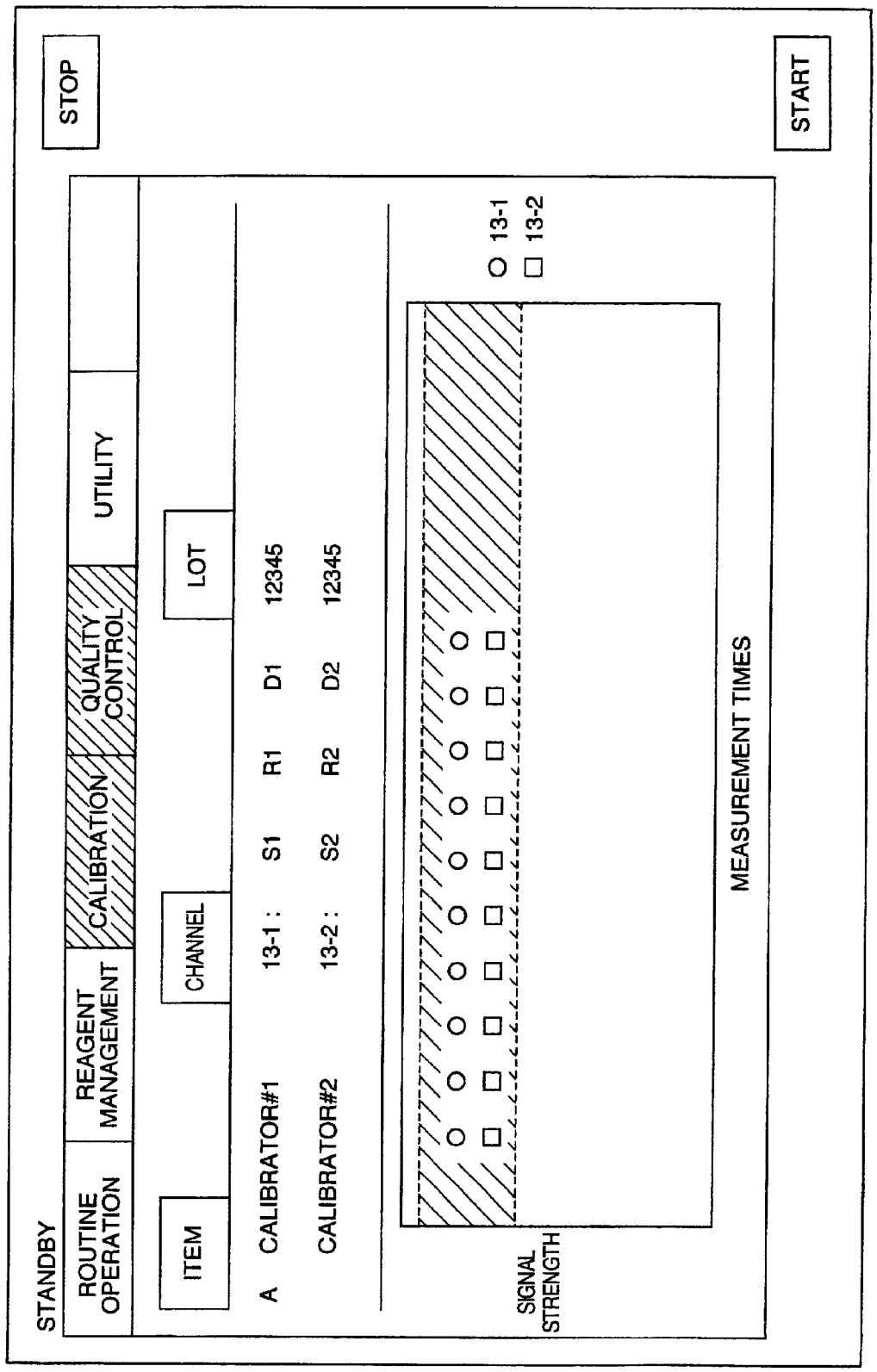
FIG. 3 is a diagram for indicating a display example of calibration information of two measurement channels in the automatic analysis apparatus shown in FIG. 1.

Also, in FIG. 3, a structure of a measurement channel is displayed in combination with calibration information. This structure clearly indicates such an element which constitutes a measurement channel and may predict a large influence given to a measurement result. For example, this structure clearly indicates that which portions of the detection units (D1, D2) for measuring a signal derived from a sample pipetting mechanism (S1, S2), a signal derived from a reagent pipetting mechanism (R1, R2), and a signal derived from a reaction fluid are different from each other, depending upon the measurement channels. It should be noted that in the graphic representation of the measurement time to the signal strength in FIG. 3, circular symbol indicates the measurement data of the measurement channel 13-1, and rectangular symbol shows the measurement data of the measurement channel 13-2.

When the measurements of the calibrators are accomplished to output the measurement results, if all of these measurement results can satisfy the allowable value, the calibration can be successfully formed. Thereafter, the process operation is advanced to a measurement of a quality control sample in response to an instruction of a user.

The signals which are obtained by measuring both the quality control sample and the regular examination sample are converted into density (concentration) of an examined substance based upon the calibration line formed in accordance with the above-described sequential operation, and then this converted density value is outputted to the output unit 17.

Figure 5:
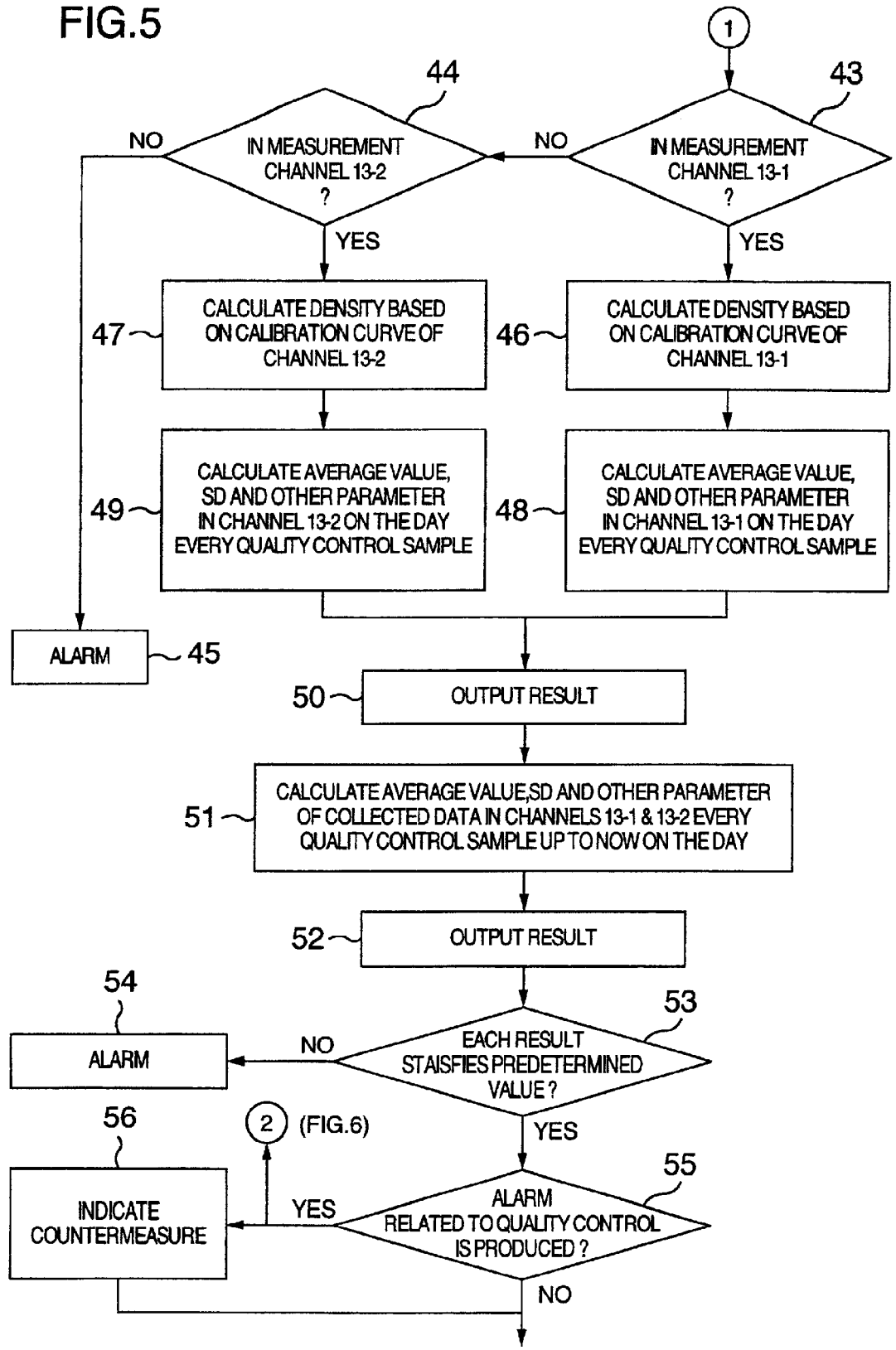
FIG. 5 is a flow chart for explaining a process flow operation of measurement data of a quality control sample in the automatic analysis apparatus represented in FIG. 1.

The quality control defined at the step 42 of FIG. 4 is carried out in accordance with a flow chart shown in FIG. 5. That is to say, in the flow chart of FIG. 5, the quality control sample is measured, and then the measurement result is judged as follows: First, a judgement is made as to whether the measurement result is obtained from the measurement channel 13-1, or the measurement channel 13-2 at a step 43 and a step 44. When it is so judged that the measurement result is obtained from neither the measurement channel 13-1, nor the measurement channel 13-2, the automatic analysis apparatus produces an alarm at a step 45.

When the quality control sample is measured in either the measurement channel 13-1 or the measurement channel 13-2, the measured signal is converted into density (steps 46 and 47). At steps 48 and 49, a statistical calculation is carried out as to quality control information related to an average value a standard deviation value, and a variable coefficient of the past measurement data for the measurement items "A" of the respective quality control samples, which have been acquired in this measurement channel on this day, and also the quality control information related to the range of the measurement data. Then, the average value and the like calculated at the steps 48 and 49 are outputted (step 50).

Subsequently, while the measurement data acquired from the respective measurement channels 13-1 and 13-2 are combined with each other without being separately distinguished, a statistical calculation is carried out with respect to the data acquired from all of the measurement channel in a similar manner to the statistical calculation executed for the data obtained from a single measurement channel, so that the quality control information as the entire automatic analysis apparatus is calculated.

In the automatic analysis apparatus of FIG. 1 according to the embodiment mode, each of the analysis modules 15-1 and 15-2 is equipped with a single measurement channel. Similarly, in such a case that an analysis module is equipped with a plurality of measurement channels, quality control information related to an average value and SD of the entire automatic analysis apparatus is calculated every measurement module and every analysis module (step 50). The resultant quality control information is outputted (step 52).

Each of the calculated values is compared with each of allowable values for quality controls (step 53). When the calculated value cannot satisfy the allowable value, this fact is displayed/outputted as an alarm (step 54). In this case, such quality control information which cannot satisfy the allowable values may be displayed/outputted, while being made in a different color distinguished from the other portion on display screen.

All of the above-described quality control information are outputted in combination with the calibration information which is employed so as to convert each of the measurement channels into the density (see FIG. 2). When the calculated value can satisfy the allowable value, a check is made at a step 55 as to whether- or not an alarm related to the quality control is issued. If such an alarm related to the quality control is not produced, then the measurement is continued. Also, at the step S55, when such an alarm related to the quality control is produced, the process result previously stored in the automatic analysis apparatus is displayed (step 56).

Similar to the above-described case of the calibration information, in the case that the quality control information which has been measured and obtained is compared with the allowable value, while a plurality of levels are previously set in the respective allowable values, a judgement may be made that the acquired quality control information is equal to which level, and the judged level may be outputted.

In the case that the automatic analysis apparatus executes the calibration in a half way while an analysis work of a certain day is carried out, in such a case that the automatic analysis apparatus performs the calibration on a half way while an inter-date difference quality control is carried out so as to measure a difference in qualities everyday, if there is a set (either analysis modules or entire analysis apparatus) of measurement channels, or such a measurement channel which may not satisfy an allowable value of a quality control, quality control information is calculated with respect to each of the measurement data whose calibration lines are identical to each other, and then, the calculated quality control information is outputted. These calibration lines are employed in the density conversion. Then, the measurement data are compared with the respective allowable values. When the measurement data cannot satisfy the allowable value, this fact is displayed/outputted as an alarm. In this case, such precision management information which cannot satisfy the allowable value may be displayed/outputted in different colors from the colors of the peripheral display contents.

FIG. 2 shows a display example of the output unit 1 which displays thereon such a list containing the calibration result obtained by the automatic analysis system shown in FIG. 1 in combination with a data list of daily quality control information acquired in an analysis work per 1 day. In this list, in addition to the calibration information in the respective measurement channels of the measurement item "A", with respect to the measurement data of the quality control samples #1 and #2, there are represented the quality control information in the respective measurement channels 13-1 and 13-2, and furthermore the quality control information for combining the measurement data of the two measurement channels with each other as the entire automatic analysis apparatus.

That is, the display example shown in FIG. 2 displays thereon: a measurement item 70; a day/time 71 when a calibration is carried out; a title 72 of calibration; a name of a quality control sample; a sort/lot 73 of a reagent; a value 74 of a signal obtained by measuring a calibration; an allowable value 75; a quality average value 76; a management SD (standard deviation) 77; a total number of measurement data; an average value of measurement data; a standard deviation of measurement data, and the like.

In the display example of FIG. 2, assuming now that the density of the quality control sample (control) is selected to be the reference value of density ±[2×(reference value of management SD)], and also the reference of the quality control is selected to be the reference value of the management SD, for example, the reference value of the density quality control in the quality control sample #1 is equal to 10 ±(2×0.5)=9 to 11, and furthermore, the quality control reference value of the management SD is less than 0.5. As a consequence, the density of the measurement channel 13-1 is selected to be 10.1 and the density of the measurement channel 13-2 is selected to be 9.0. Since an average value of the entire density is equal to 9.6, any one of the above-explained density is the management reference value.

Also, since the management SD of the measurement channel 13-1 is equal to 0.1 and the management SD of the measurement channel 13-2 is equal to 0.4, and furthermore, the average value of the entire management is equal to 0.7, the respective measurement channels are less than the quality control reference value. However, the overall management SD is outside the quality control reference value. In this case, the value exceeding the allowable value, namely the entire management SD of the quality control 1 is displayed in a different color from the color of the peripheral display content.

Also, in the display example shown in FIG. 2, a signal value "96" of the calibrator #1 in the measurement channel 13-2 is present at a boundary of an allowable range 65–105, and may be discriminated from, for example, a level 2 (low). As a result, it can be understood that the inclination of the calibration line becomes small, as compared with that of the measurement channel 13-1. In this case, the user may take such a measure of increasing the signal gain, for example, the signal value of the calibrator #1 of the measurement channel 13-2.

Alternatively, various countermeasures such as maintenance items are previously stored by combining such cases that the quality control information of the measurement channel, the analysis module, or the entire analysis apparatus cannot satisfy the allowable values, and also by combining the respective levels of the calibration information in these cases. Then, when each of the quality control information cannot satisfy the allowable value, this stored solution process corresponding thereto may be outputted.

Figure 6:
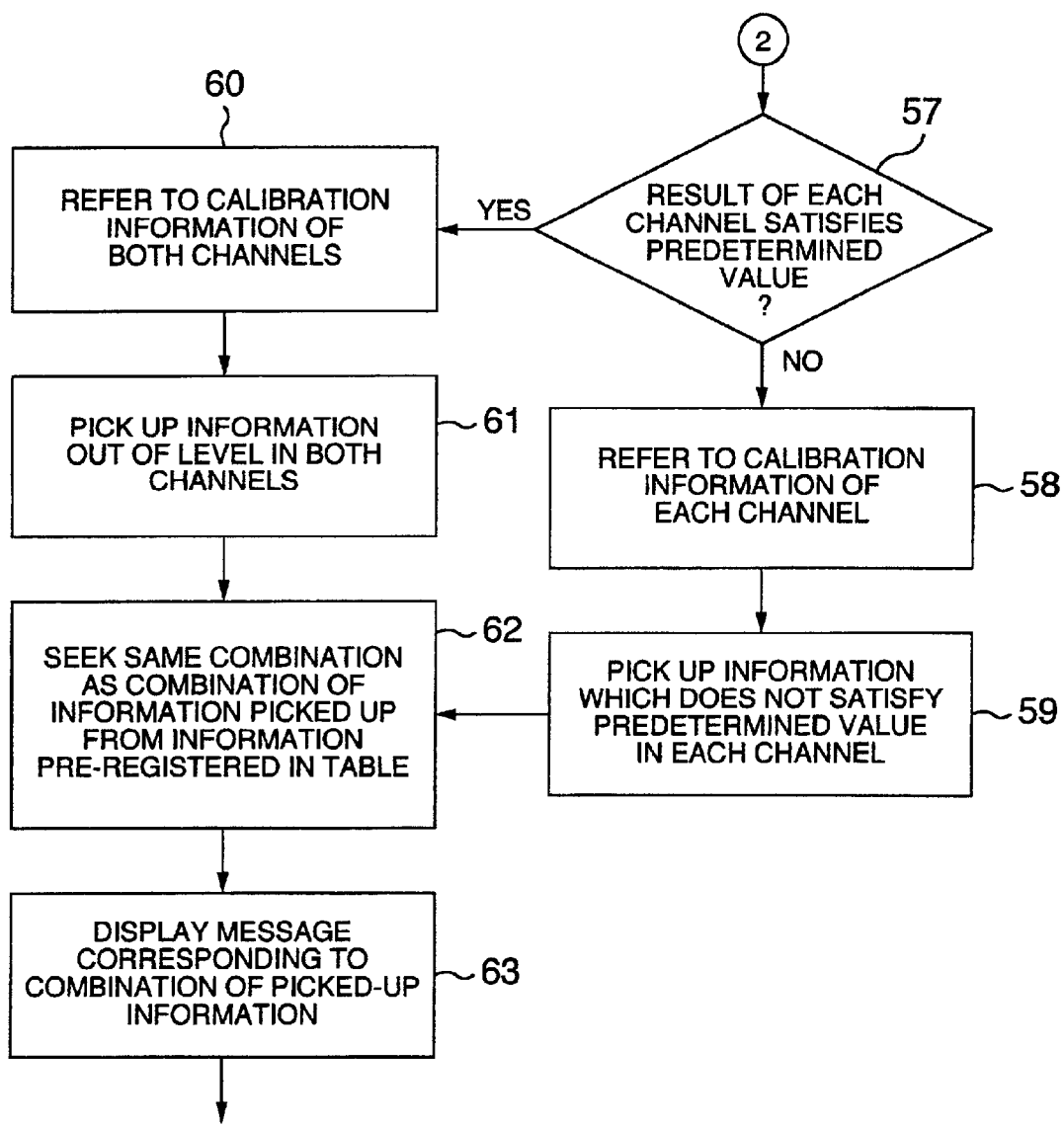
FIG. 6 is a flow chart for describing a process flow operation for displaying a process operation in the case that the display result of FIG. 2 is obtained in the automatic analysis apparatus indicated in FIG. 1.

FIG. 6 is a flow chart for describing a process flow operation in such a case that, for example, when the results as indicated in the display example of FIG. 2 are obtained in the analysis system of FIG. 1, post-measure steps are displayed.

First, in the flow process operation of FIG. 6, a judgement is made as to whether or not a quality control result obtained in each of the measurement channels is out of the quality control (step 57). In this case, as the respective measurement channels in the measurement channels 13-1 and 13-2, the respective allowable values can be satisfied. However, an average SD (standard deviation) of two totalized channels of the quality control sample #1 cannot satisfy the allowable value. As a result, the analysis system refers to the calibration information of both the measurement channels 13-1 and 13-2 (step 60). Then, as to each of the information obtained from both the measurement channels, information having a different level from other levels is picked up (step 61). It is now assumed at this step 61 that the information to be picked-up may also involve such information about the different calibrator and the different lot of the reagent.

In this display example of FIG. 2, all of the calibration information acquired from the measurement channel 13-1 are the level 1, and a ratio of the calibrator #1 of the measurement channel 13-2 to the calibrator #2 thereof is the level 2 (low).

A table is previously prepared and is previously stored in a memory of the data processing unit 16. This table represents a plurality of instruction messages with respect to all of combinations between the data items of the quality control information which cannot satisfy the allowable value and the level values of the calibration information. An example of this table is indicated in FIG. 7. Referring to this table, such a combination is sought which is the same as the combination between the data item of the quality control information which cannot satisfy the present allowable value and also the level value of the calibration information (step 62). Then, each instruction message 80 corresponding to a combination of the picked-up information may be printed out from a printer, or may be displayed/outputted on an display screen (step 63). For instance, such a message is displayed by which a process operation of "maintenance #1" is carried out with respect to the measurement channel 13-2.

When the results of the respective measurement channels do not satisfy a preselected value, the process operation is advanced to a step 58. At this step 58, the CPU refers to the calibrations information of each of the measurement channels. Then, the process operation is advanced to a further step 59. At this step 59, the data which do not satisfy a predetermined reference value in each of the measurement channels is picked up. Subsequently, the process operation is advanced to a step 62.

As previously explained, when the quality control information as the entire automatic analysis apparatus, which is obtained by combining the measurement data of the two measurement channels with each other, is out of the quality control, if the calibration information staged by the respective measurement channels can be observed in the same table (same screen), then the conditions of the measurement channels can be easily grasped.

In other words, in accordance with one embodiment mode of the present invention, in the automatic analysis apparatus having a plurality of measurement channels, the measurement quality of each of the measurement channels is calculated so as to be displayed. Moreover, the measurement quality of the entire apparatus in which the respective measurement channels are combined with each other is calculated and also displayed. As a consequence, the user can recognize such a case that although the measurement quality allowable range can be satisfied in the respective measurement channels, the measurement quality allowable range cannot be satisfied in the entire analysis apparatus.

Also, since the calibration information of the respective channels is additionally displayed, the condition of the automatic analysis apparatus can be grasped.

Furthermore, in such a case that although the measurement quality allowable range can be satisfied in the respective measurement channels, the measurement quality allowable range cannot be satisfied in the entire analysis apparatus, such a display is made. That is, which measurement channel is processed by executing which type of maintenance. As a result, the measurement quality control of the automatic analysis apparatus can be readily carried.

In other words, not only the respective quality control information of the plural measurement channels owned by a single set of automatic analysis apparatus is judged to be displayed, but also the quality of the overall analysis apparatus is judged to be displayed. As a consequence, such an automatic analysis apparatus capable of improving the measurement quality control can be realized.

As previously described, in accordance with the present invention, no only the respective quality control information of the plural measurement channels owned by a single set of automatic analysis apparatus is judged to be displayed, but also the quality of the overall analysis apparatus is judged to be displayed. As a consequence, such an automatic analysis apparatus capable of improving the measurement quality control can be realized.

As a result, it is possible to improve the efficiency of the reliability confirmation for acquiring such data whose quality is stable even when the measurement is carried out in any of the measurement channels.

What is claimed is:

1. An automatic analysis apparatus for measuring a reaction on reagent and a sample put into a reaction container, comprising:

a plurality of measurement channels, each of said measurement channels including said reaction container and means for measuring said reaction;

data processing means for producing calibration information, first quality control information, and second quality control information, said calibration information for every measurement channel being produced based upon calibration data obtained by measuring a calibration sample, said calibration information including at least measurement data of the calibration sample, said first quality control information including at least measurement data of a quality control sample and related to a quality for each of said measurement channels being produced based upon measurement data acquired by measuring the quality control sample by the respective measurement channels, and also said second quality control information including at least a standard deviation value which is calculated based on a group of measurement data obtained by measuring the quality control sample for a same measurement item in a plurality of measurement channels and by a same manner as obtained from a single measurement channel; and display means for simultaneously displaying said calibration information, said first quality control information, and said second quality control information given by said data processing means on a same screen.

2. An automatic analysis apparatus as claimed in claim 1, wherein said display means simultaneously displays said calibration information, said first quality control information, and said second quality control information on the same screen with respect to each of measurement items.

3. An automatic analysis apparatus as claimed in claim 1, wherein said data processing means sets each of preselected allowable values with respect to said calibration information, said first quality control information, and said second quality control information.

4. An automatic analysis apparatus as claimed in claim 3, wherein said data processing means includes:

means for judging as to whether or not the calibration information of each of said measurement channels can satisfy said allowable value; and means for setting a level value corresponding to deviation of said calibration information from said allowable value in the case that said calibration information can satisfy said allowable value.

5. An automatic analysis apparatus as claimed in claim 3, wherein said data processing means includes:

means for judging as to whether or not both said first quality control information and said second quality control information satisfy the respective allowable value thereof; and means for setting a level value corresponding to a deviation value of said second quality control information from said allowable value thereof in the case that both said first quality control information and said second quality control information satisfy the respective allowable value thereof.

6. An automatic analysis apparatus as claimed in claim 4, wherein said display means displays thereon said calibration information in a display mode corresponding to said level value and discriminatable from other display information in such a case that said calibration information satisfies said allowable value thereof.

7. An automatic analysis apparatus as claimed in claim 5, wherein said display means displays thereon said first and second quality control information in display modes corresponding to said level values and discriminatable from other display information in such a case that said first and second quality control information satisfy said allowable values thereof.

8. An automatic analysis apparatus as claimed in claim 3, wherein said data processing means includes:

a table made by that a message for designating a sort of a maintenance process of said automatic analysis apparatus is set in correspondence with a combination between any one of said first and second quality control information which do not satisfy said allowable values thereof, and the level value of said calibration information;

means for judging as to whether or not any one of said first and second quality control information satisfies said allowable value thereof; and means operable in that when any one of said first and second quality control information does not satisfy said allowable value thereof, said means refers to said table so as to read out a sort of a maintenance process corresponding to such a combination between a present level value of said calibration information and any one of said first and second quality control information which do not satisfy said allowable values thereof.

9. A management apparatus for managing an automatic analysis apparatus having a plurality of measurement channels used to measure reaction occurred between a reagent and a sample, comprising:

data processing means for producing calibration information, first quality control information, and second quality control information; said calibration information for every measurement channel being produced in each of said measurement channels based upon calibration data obtained by measuring a calibration sample, said calibration information including at least measurement data of the calibration sample, said first quality control information including at least measurement data of a quality control sample and related to a quality for each of said measurement channels being produced based upon measurement data acquired by measuring a quality control sample by the respective measurement channels, and also said second quality control information including at least a standard deviation value which is calculated based on a group of measurement data obtained by measuring the quality control sample for a same measurement item in a plurality of measurement channels and by a same manner as obtained from a single measurement channel; and display means for simultaneously displaying said calibration information, said first quality control information, and said second quality control information given by said data processing means on a single screen.

10. A computer program product comprising:

a computer usable medium having computer readable program code means embodied therein for managing an automatic analysis apparatus containing a plurality of measurement channels used to measure reaction occurred between a reagent and a sample, wherein:

said computer readable program code means is comprised of:

data processing means for producing calibration information, first quality control information, and second quality control information; said calibration information for every measurement channel being produced based upon calibration data obtained by measuring a calibration sample, said calibration information including at least measurement data of the calibration sample, said first quality control information including at least measurement data of a quality control sample and related to a quality for each of said measurement channels being produced based upon measurement data acquired by measuring the quality control sample by the respective measurement channels, and also said second quality control information including at least a standard deviation value which is calculated based on a group of measurement data obtained by measuring the quality control sample for a same measurement item in a plurality of measurement channels and by a same manner as obtained from a single measurement channel; and display means for simultaneously displaying said calibration information, said first quality control information, and said second quality control information given by said data processing means on a single screen.

11. An automatic analysis apparatus for measuring a reaction on reagent and a sample put into a reaction container, comprising:

a plurality of measurement channels, each of said measurement channels including said reaction container and means for measuring said reaction;

data processing means for producing calibration information, first quality control information, and second quality control information, said calibration information for every measurement channel being produced based upon calibration data obtained by measuring a calibration sample, said calibration information including at least measurement data of he calibration sample, said first quality control information including at least measurement data of a quality control sample and related to a quality for each of said measurement channels being produced based upon measurement data acquired by measuring the quality control sample by the respective measurement channels; and also second quality control information including at least a standard deviation value which is calculated based on a group of measurement data obtained by measuring the quality control sample for a same measurement item in a plurality of measurement channels and by a same manner as obtained from a single measurement channel, and display means for simultaneously displaying said calibration information and said first quality control information given by said data processing means on a same screen.

* * * * *